United States Patent [19]
Licata et al.

[11] Patent Number: 5,951,518
[45] Date of Patent: Sep. 14, 1999

[54] INTRODUCING DEVICE WITH FLARED SHEATH END

[75] Inventors: Michael J. Licata, Jaffrey, N.H.; Elizabeth Hunt, Winchendon, Mass.; John Grubis, Rindge, N.H.

[73] Assignee: Teleflex, Incorporated, Plymouth Meeting, Pa.

[21] Appl. No.: 08/961,971

[22] Filed: Oct. 31, 1997

[51] Int. Cl.⁶ .................................................. A61M 5/178
[52] U.S. Cl. .......................................... 604/161; 604/164
[58] Field of Search ................................. 604/160, 161, 604/164, 165, 264, 280, 283

[56] References Cited

U.S. PATENT DOCUMENTS

| | | | |
|---|---|---|---|
| 862,712 | 8/1907 | Collins . | |
| 3,537,451 | 11/1970 | Beck et al. | 604/165 |
| 3,788,326 | 1/1974 | Jacobs | 128/305 |
| 3,860,006 | 1/1975 | Patel | 128/347 |
| 3,921,631 | 11/1975 | Thompson | 128/214.4 |
| 4,147,165 | 4/1979 | Tauchinski | 128/214.4 |
| 4,168,709 | 9/1979 | Bentov | 128/345 |
| 4,233,974 | 11/1980 | Desecki et al. | 604/165 |
| 4,243,050 | 1/1981 | Littleford | 128/784 |
| 4,471,778 | 9/1984 | Toye | 604/160 |
| 4,585,013 | 4/1986 | Harris | 128/785 |
| 4,596,559 | 6/1986 | Fleischhacker | 604/170 |
| 4,772,266 | 9/1988 | Groshong | 604/164 |
| 4,793,363 | 12/1988 | Ausherman et al. | 128/754 |
| 4,834,708 | 5/1989 | Pillari | 604/165 |
| 4,883,468 | 11/1989 | Kousai et al. | 604/161 |
| 4,966,588 | 10/1990 | Rayman et al. | 604/165 |
| 4,983,168 | 1/1991 | Moorehead | 604/161 |
| 4,997,424 | 3/1991 | Little | 604/161 |
| 5,064,414 | 11/1991 | Revane | 604/168 |
| 5,098,392 | 3/1992 | Fleischhacker et al. | 604/165 |
| 5,141,497 | 8/1992 | Erskine | 604/160 |
| 5,147,336 | 9/1992 | Wendell et al. | 604/283 |
| 5,160,323 | 11/1992 | Andrew | 604/165 |
| 5,163,903 | 11/1992 | Crittenden et al. | 604/96 |
| 5,167,634 | 12/1992 | Corrigan, Jr. et al. | 604/161 |
| 5,221,263 | 6/1993 | Sinko et al. | 604/161 |
| 5,250,033 | 10/1993 | Evans et al. | 604/161 |
| 5,275,583 | 1/1994 | Cranich | 604/264 |
| 5,279,597 | 1/1994 | Dassa et al. | 604/165 |
| 5,290,294 | 3/1994 | Cox et al. | 604/164 |
| 5,334,157 | 8/1994 | Klein et al. | 604/160 |
| 5,380,293 | 1/1995 | Grant | 604/177 |
| 5,391,152 | 2/1995 | Patterson | 604/165 |
| 5,437,645 | 8/1995 | Urban et al. | 604/165 |
| 5,489,273 | 2/1996 | Whitney et al. | 604/160 |
| 5,741,233 | 4/1998 | Riddle et al. | 604/165 |
| 5,782,807 | 7/1998 | Falvai et al. | 604/164 |

FOREIGN PATENT DOCUMENTS

WO 93/13822   7/1993   WIPO .

OTHER PUBLICATIONS

TFX Medical Product Literature for T–Peel™ Peelable Introducers.
Quinton Instrument Co. Literature.
B. Baun Medical Inc. Literature.

Primary Examiner—Wynn Wood Coggins
Assistant Examiner—Sharon Finkel
Attorney, Agent, or Firm—David G. Conlin; Peter F. Corless; Dike, Bronstein, Roberts & Cushman, LLP

[57] ABSTRACT

An improved percutaneous introducer device is provided that provides a splittable sheath having a flared lead in for the facile introduction of ancillary medical implements, such as small diameter catheters, guide wires and the like, and a hub member being shaped to matingly underlie the flared lead in. When the hub is separated, such as by wings being pulled apart radially to the sheath, the sheath is longitudinally split, allowing it to be easily removed from an in situ catheter.

8 Claims, 2 Drawing Sheets

INTRODUCING DEVICE WITH FLARED SHEATH END

BACKGROUND OF THE INVENTION

1. Field of the Invention

The present invention relates to an introducer device for insertion of a catheter, guide wire and the like into a patient. More particularly, the invention provides an improved introducer device comprising a splittable sheath component wherein the sheath comprises a flared end that significantly facilitates entry of a catheter, guide wire, etc. into the device.

2. Background

Splittable introducer devices have been employed for inserting catheters, guide wires and the like into patients. A typical procedure provides for insertion of a dilator or needle encased within a splittable sheath into the vasculature of a patient. After insertion, the dilator or needle may be removed leaving the sheath protruding from the patient's vein. A diagnostic or therapeutic catheter (e.g. a central venous access catheter or guide wire) or other object such as a capsule is then threaded through the sheath into the patient. The encasing sheath is then longitudinally sheared and removed from the catheter or guide wire and the patient such as by applying opposing force to opposed wings or tabs of the introducer device. See U.S. Pat. Nos. 5,334,157; 5,221,263; 5,141,497; 5,098,392; 4,772,266; and 4,243,050; and WO 97/14456 and WO 97/14468.

It can be quite difficult for the surgeon or other medical personnel to insert a catheter or guide wire into an introducer device, particularly when using a small diameter catheter or guide wire. For example, very small diameter catheter are employed in many applications, such as catheters having a diameter of 0.026 inches or less that are used for insertion into the vasculature of neonatal patients. To introduce such a small, flexible tube into the small bore of the introducer requires that the attending medical personnel to exercise significant manual dexterity.

Certain prior introducer devices have been reported that include a hub or wing portions that contain a conical-type lead-in section that could facilitate entry of a guide wire or catheter into the bore of the device's sheath. In those prior devices, the sheath component is affixed to some point along the longitudinal axis and interior surface of the hub or wing portion(s) of the device. The top proximal end of the sheath necessarily forms a shoulder or flange within the hub or wing portion(s), which flange can inhibit a catheter or guide wire passing through the device, particularly the leading edge of a catheter or guide wire. Such inhibition can cause bending of the catheter or guide wire that requires the ancillary medical device to be removed and then reinserted into the introducer. At a minimum, such inhibition of an ancillary medical device is annoying and inconvenient to the medical personnel.

Thus, it would be desirable to have a new introducer device that facilitates entry of an ancillary medical device such as a catheter, guide wire or the like into the device.

SUMMARY OF THE INVENTION

The present invention comprises an improved introducer device. The device has a sheath component that has a flared, preferably substantially conical-shaped end forming a lead-in section for facile introduction of an ancillary medical device, such as a catheter, guide wire, or the like. The sheath is typically adapted to snugly receive a dilator or needle for insertion in a vein or artery of a patient while circumscribed by the sheath.

We have found that design affords substantial advantages. In particular, a continuous introduction pathway is provided from the flared end into the lumen or bore of the introducer sheath that does not have any surface features that can arrest the forward travel of the end of an advancing catheter, guide wire or other ancillary medical device that may be inserted through the sheath. Additionally, the sheath may be secured to the full length of attached wing portions, providing a relatively increased surface area of attachment of the sheath to the wing portions, thereby providing more affirmative splitting of the sheath.

In a preferred aspect, the introducer device of the invention includes: 1) a sheath component comprising a bore and a flared introduction end, the sheath preferably being capable of being axially sheared and adapted to receive a dilator or percutaneous needle for insertion into a vein or artery of a patient while circumscribed by the sheath; 2) a hub unit attached to the sheath, the hub preferably comprising two opposed wing portions attached to the sheath, the wing portions capable of splitting the sheath upon application of an effective shearing force to the wing portions; and 3) a dilator or needle for insertion into selected vasculature of a patient while circumscribed by the sheath.

Preferably the wing portions of the device are disposed diametrically opposed to one another, each wing portion forming half of a lead-in section that can facilitate entry of a catheter, guide wire or other ancillary medical device. The hub unit underlies the sheath lead-in portion, and that sheath lead-in portion may be physically attached to the hub portion such as by an adhesive e.g. a cyano-based adhesive. The sheath lead-in portion also may be unattached to the underlying hub unit.

In a further preferred aspect, an introducer device is provided that includes a sheath component comprising a bore adapted to receive a hollow dilator or needle at a flared end thereof for insertion into vasculature of a patient while circumscribed by the sheath, and a hub unit attached thereto, capable of splitting the sheath upon application of an effective shearing force to the hub via, for example, the wing portions; and wherein the hub unit forms a lead-in section that substantially matingly underlies the flared portion of the sheath. Such arrangement aids insertion of a catheter or other ancillary medical device into the bore of the sheath.

It is further preferred that the wing portions do not completely circumscribe the hub or the sheath component, but rather the wing portions are non-integral components that are separated, preferably on each of opposing sides, by the underlying sheath. By this configuration, the wing portions are not split during shearing of the sheath, i.e. the sheath can be sheared along score lines formed in the surface interposed between the separated wing portions, thereby facilitating the shearing process.

Methods of the invention include means for inserting a guide wire, catheter or other ancillary medical device into selected vasculature of a patient that comprises piercing a selected vein or artery of a patient with an introducer device of the invention; withdrawing a needle or dilator of the introducer device from the sheath component and inserting a catheter or guide wire through the sheath component; and applying outwardly cooperating forces to the wing portions to thereby axially shear the sheath.

Other aspects of the invention are discussed infra.

DETAILED DESCRIPTION OF ILLUSTRATIVE EMBODIMENTS

As stated above, an improved introducer device is provided that contains a sheath component that has a flared proximal end that extends upwardly and above the proximal end of an attached hub component wherein that flared sheath proximal end provides a convenient lead-in section for entry of a dilator or percutaneous needle as well as ancillary medical devices inserted through the sheath such as a catheter or guide wire. In accordance with conventional practice, "proximal end" designates herein the specified end closest to the medical personnel manipulating the introducer device, and "distal end" designates the specified end closest to the patient.

Also, as used herein, "flared" proximal sheath end generally refers to a terminal portion of the sheath having an outwardly extending opening that is of greater diameter than the sheath body. In particular, a flared sheath end may suitably have a convex shape, such as a taper. More typically, the flared end may be formed as a conical funnel end with an inside diameter graduating from an open end to the diameter of the sheath as generally shown in the figures.

Figure 1A:
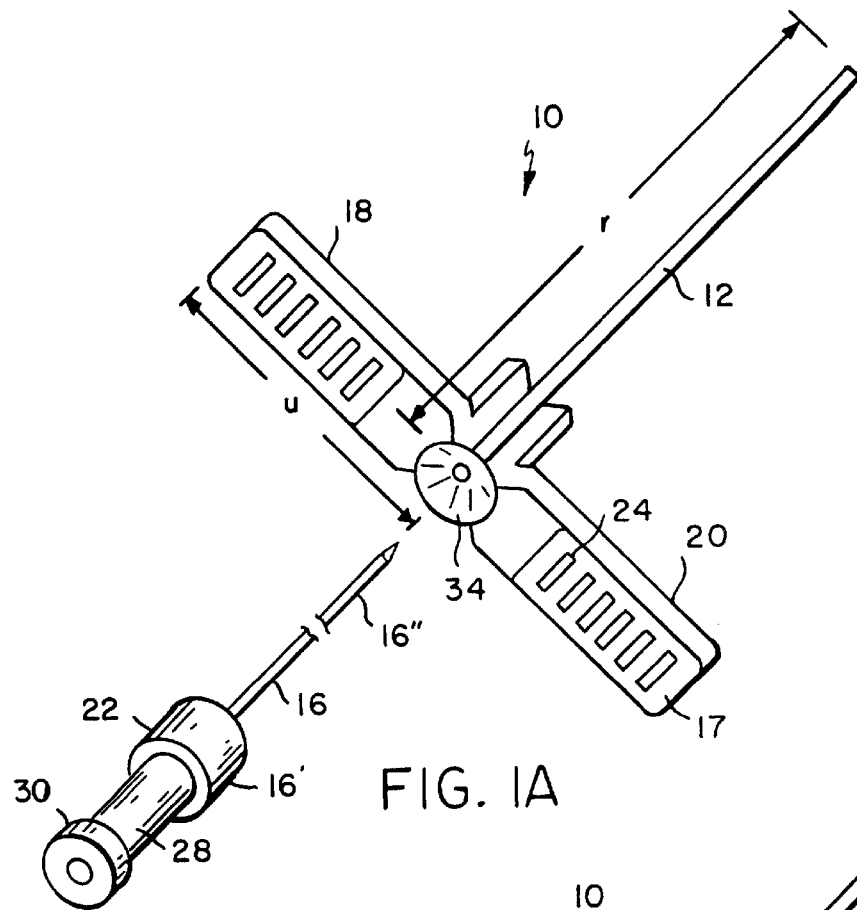
FIG. 1A shows an above view of separated splittable sheath and needle components of a preferred introducer device of the invention.
Figure 1B:
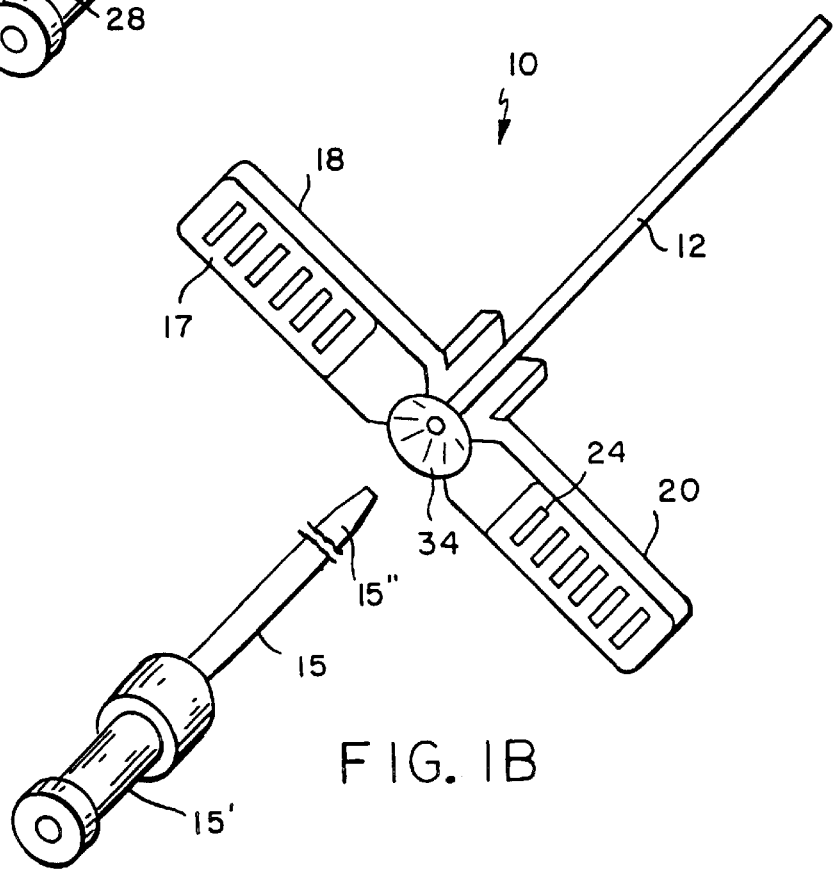
FIG. 1B shows an above view of separated splittable sheath and dilator components of a further preferred introducer device of the invention.
Figure 3:
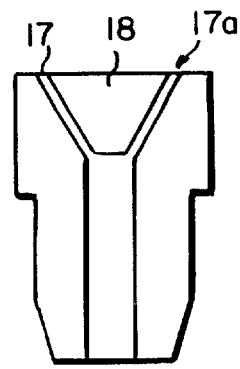
FIG. 3 shows a side view of a wing portion of one aspect of the instant invention forming a hub of an introducer device according to the invention.

Referring now in detail to the Drawings, where preferred illustrative introducer devices of the invention are depicted, FIG. 1A shows introducer device 10 that includes splittable sheath component 12 having a bore 14 adapted to receive hollow needle 16 that is inserted into a selected vein or artery of a patient. As discussed above, a hollow dilator also could take the place of needle 16, as shown in the corresponding device 10 of FIG. 1B. A hub unit 17, as shown in FIGS. 1A, 1B and 3, is preferably formed as a convex shape for matingly underlying the flared end of the sheath and attached thereto when assembled. Two opposed wing or tab portions 18 and 20 are attached to the hub 17. The wing portions 18 and 20 may be diametrically opposed to each other as depicted in FIGS. 1A and 1B.

In the illustrative embodiment, the wings 18, 20 are substantially L-shaped, and when mounted in diametrically opposed fashion on the sheath 12, result in a T-shaped configuration for the introducer 10. While such an L-shape is preferred, wing portions of other shapes could be employed. For example, the wing portions each could be angled (together substantially V-shaped, creating a Y-shaped introducer) or outwardly rounded, provided the wing portions could be engaged to effect shearing of the sheath component as desired.

Figure 4:
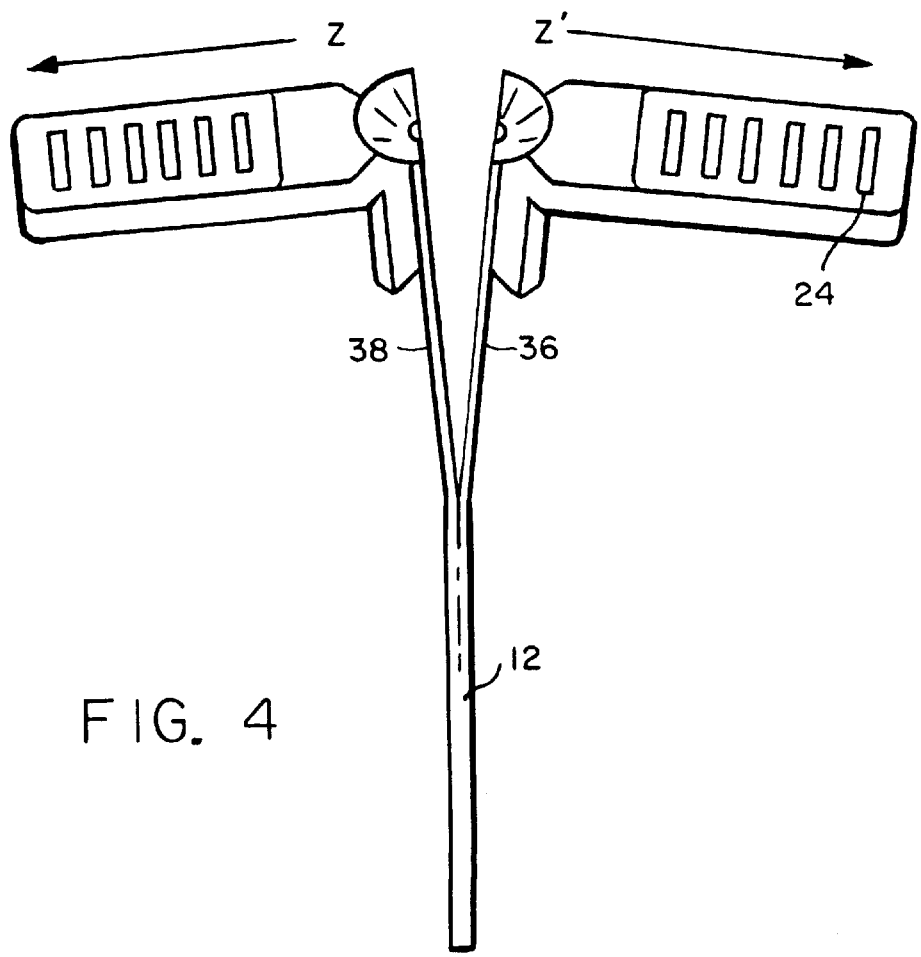
FIG. 4 shows a perspective view of an introducer device of the invention illustrating the splitting of the sheath.

It is also preferred that the outer surface of wing portions 18 and 20 include topography to aid handling and manipulation of the introducer device. In particular, and as shown in FIGS. 1A, 1B and 4, preferably the exposed sides of wing portions 18 and 20 have ridged gripping surfaces 24 or have other topography to facilitate handling and manipulation of device 10.

As shown in FIG. 1A, a needle body portion 22 is attached to the proximal end 16' of hollow needle 16. Preferably the needle body portion includes an open-ended flash chamber 28 that receives blood flowing upward through bored needle 16 when sharpened distal end 16" pierces a patient's vein, thereby informing the medical personnel the needle has been successfully inserted. The distal end of needle body portion 22 includes a narrow bore that is adapted to firmly engage needle 16. At the needle proximal end 16', a bore within needle body portion 22 expands to form flash chamber 28. The flash chamber may be molded of transparent material, e.g., plastic.

Preferably the distal portion of needle body portion 22, on the side opposite that from which wing portions 18, 20 outwardly extend, tapers inward to provide an inset or flatter profile. This configuration enables the device to be more securely and conveniently placed on a patient (e.g. on the patient's forearm), and also facilitates access to and manipulation of proximal ends of needle 16 and needle body portion 22 by medical personnel. It is particularly preferred that the needle body portion taper commences at a position proximate to needle proximal end 16' as shown in FIG. 1A.

Preferably a top lip 30 with luer threads is formed on the outer surface of the proximal end of needle body portion 22 and is adapted to receive a syringe for administration to a patient via needle 16. Flash chamber 28 may also include a luer taper within needle body portion 22.

Sheath 12 includes a flared proximal end forming a lead-in section 34, preferably tapered or substantially cone shaped as shown in FIG. 3, and which aids insertion of a catheter, guide wire or the like into the bore of the splittable sheath. Preferably hub 17 comprises a convex sloping portion having a shape matingly underlying the lead-in section 34, as can be seen clearly in FIG. 2.

It is preferred that wing portions 18 and 20 are non-integral components, i.e. wings 18 and 20 are unattached with respect to each other, preferably separated on each of opposing sides by the underlying splittable catheter portions 36 and 38 as can be seen in FIG. 4. As discussed above, by this configuration, the wing portions are not split during shearing of the sheath, thereby facilitating the shearing process. Nevertheless, if desired, wing portions 18 and 20 could be attached and thereby circumscribe portions 36 and/or 38 as well as the rest of the periphery of the splittable sheath. For such a design, the wing portions should include suitable means for shearing of the attached wing portions upon shearing of the sheath component, e.g. the attached wing portions could include a scored or otherwise weakened surface(s) axially aligned with intended lines of shearing 42, 44 of the sheath.

Preferably splittable sheath 12 and lead-in 34 include axially extending, diametrically opposed score lines 40 and 42 to facilitate axial shearing upon imparting opposing divergent forces on wing portions 18 and 20. Score lines 40 and 42 should each traverse interposed portions 36 and 38, including the flared portions forming lead in 34.

As mentioned above, FIG. 1B shows a preferred introducer device of the invention, which is generally similar to the introducer device shown in FIG. 1A, except that a dilator 15 with distal tip 15" and proximal end hub 15' is employed and inserted through the sheath 12 during use of the device instead of a needle 16 as in the device of FIG. 1A. It is understood that elements of the device of FIG. 1B also depicted in FIG. 1A are identified with corresponding reference numerals in FIG. 1B. Additionally, those elements, and preferred aspects thereof, are the same for the device of FIG. 1B as described above for the device of FIG. 1A.

Figure 2:
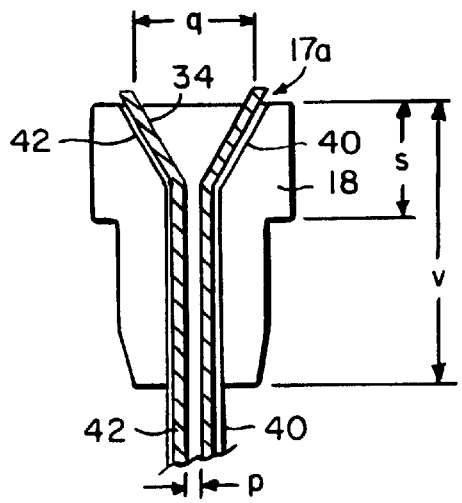
FIG. 2 shows a cut-away side view of an introducer device according to the invention.

Suitable dimensions of the components of an introducer device of the invention can suitably vary rather widely and can be readily determined by those skilled in the art based on the present disclosure. In general, splittable sheath 12 and needle 16 or dilator 15 should have a diameter capable of being inserted within selected vasculature of a patient, and sheath 12 should have a diameter sufficient to accommodate a catheter, guide wire or the like. In general, with reference to the device depicted in FIG. 1A, preferably the diameter of splittable sheath 12 is between about 1 mm and 2.5 mm; and the diameter of needle 16 is between about 0.7 mm and 2 mm. Preferably the overall length of introducer device 10 of FIG. 1A is between about 30 mm and 45 mm, with splittable sheath 12 extending between about 10 or more mm below the wing portions 18, 20. The lead in 34 flared end may optionally extend slightly above the hub edge 17 as depicted in FIG. 2, or it may not extend above the hub edge 17a. The length of needle 16 may be between about 30.5 mm and 46 mm. The graduating lead-in portion may suitably comprise from about 1 to 10 percent of the total length of the sheath, more typically about 2 to 6 percent of the sheath total length, although lead-in portions of a variety of lengths will be suitably. The lead-in portion may suitably expand to a maximum diameter (at the lead-in portion proximal end) that is from about 1.5 to about 2, 3 or 4 times the diameter of the sheath (e.g. the diameter of the sheath as measured at the midpoint of the sheath length), although again lead-in portions of a variety of maximum diameters will be suitable to provide facilitated entry of needles, dilators, guide wires, catheters, etc.

In one preferred introducer device of the invention adapted to receive a percutaneous needle and generally corresponding to the device shown in FIGS. 1A and 2 of the drawings, the diameter of the sheath (diameter p shown in FIG. 2) is about 2 mm; the maximum diameter of the sheath lead-in portion (diameter q in FIG. 2) is 5 mm; the length of the sheath including the lead-in portion (length r in FIG. 1A) is 4 cm; the length of the lead-in portion (length s in FIG. 2) is 3 mm; the width of a wing portion (width u in FIG. 1A) is 1.6 cm; and the length of a wing portion (width v in FIG. 2) is 1 cm.

With respect to the device depicted in FIG. 1B, wherein the sheath encases dilator rather than a sheath, devices of substantially greater dimensions will be usable, e.g. a device that is from 15 to 20 inches or more in length depending on the intended application, as will be appreciated by those skilled in the art upon consideration of this disclosure. Also, the diameters of a dilator as well as a sheath for circumscribing the dilator will be greater than the corresponding diameters of a device that employs a percutaneous needle instead of a dilator.

The components of an introducer device of the invention may be from a number of materials as will be appreciated by those skilled in the art. For example, the sheath and hub unit each are suitably formed from a polyethylene. The sheath (which includes the lead-in portion) is preferably from a fluorinated ethylene-propylene resin (FEP), and also could be formed from other fluorinated resins, e.g. a tetrafluoroethylene polymer such as TEFLON. A hollow needle 16 is suitably fabricated from stainless steel as is known in the art. The needle body portion 22 may be suitably rigid plastic such as a polyethylene, preferably with extended chamber 28 being substantially transparent so blood received therein can be readily observed. A dilator 15 may be suitably formed from a polyethylene. A dilator 15 is preferably formed from a fluorinated ethylene-propylene resin (FEP), and also could be formed from other fluorinated resins, e.g. a tetrafluoroethylene polymer such as TEFLON. The sheath can be suitably formed in an insert molding process as is known in the art wherein the sheath is extruded with an expansion at one end to provide the integral lead-in portion, and then the hub unit with wing portions can be molded directly thereon.

The hub unit also can be separately formed and then attached, such as by a suitable adhesive. It is also possible to interpose a mounting unit such as a plastic strip between the hub unit and the sheath, although such an arrangement is generally less preferred.

An introducer device of the invention may be suitably used as follows for placement of a catheter, guide wire or the like in a patient. A needle 16 or dilator 15 is inserted into lead-in 34 such that tip sheath 16" or dilator tip 15" extends from the bore of the sheath 12 and a distal end thereof. The introducer device 10 is inserted into a selected patient. If a needle 16 is employed, insertion of sharpened distal needle end 16" into a patient may be verified by blood flashback observed in chamber 28. Dilator 15 may be suitably inserted into selected vasculature that has already been penetrated by another medical device. Needle 16 or dilator 15 with attached needle body portion 22 suitably then may be withdrawn from the sheath 12, which remains in the vein or artery of the patient. A catheter or other medical device then can be introduced into lead-in 34 and threaded through the sheath component and into the vasculature. After desired placement of the catheter or other medical device, the lead-in 34 and the sheath 12 is sheared by substantially opposite outward forces applied by the fingers in the directions Z and Z' depicted in FIG. 4. That outward force operates to shear the lead in 34 and sheath 12 along the score lines thereof as discussed above.

The foregoing description of the present invention is merely illustrative thereof, and it is understood that variations and modification can be made without departing from the spirit or scope of the invention as set forth in the following claims.

What is claimed is:

1. A method of introducing a catheter or guide wire into the vasculature of a patient comprising:
   (a) providing a medical introducer device that comprises
      (i) a sheath having a proximal end and a distal end and a bore adapted to receive a dilator or needle, the sheath having a flared lead-in portion for aiding the introduction of ancillary medical implement into the bore, the lead-in portion forming a outwardly convex shape converging and outwardly extending from an open proximal end to the bore; (ii) a hub portion underlying at least a part of the sheath lead-in portion; and (iii) a needle or dilator inserted in the sheath bore;
   (b) inserting a catheter or guide wire through the sheath into the vasculature of the patient;
   (c) applying cooperating forces to the device hub portion to axially shear the sheath.

2. The method of claim 1 wherein the hub portion comprises an outwardly convex shape that underlies the lead-in portion.

3. The method of claim 1 wherein the lead-in portion is axially scored to aid in splitting of the lead-in portion.

4. The method of claim 1 wherein the hub portion comprises wing portions and cooperating forces are applied to the wing portions to axially shear the sheath.

5. The method of claim 4 wherein the wing portions extend from the device substantially diametrically opposed to each other.

6. The method of claim 4 wherein the sheath is not completely circumscribed by the wing portions.

7. The method of claim 4 wherein the wing portions are not sheared upon shearing of the sheath.

8. The method of claim 1 wherein the hub portion comprises at least two non-integral portions which are unattached with respect to each other and are separated on opposing sides by the underlying sheath.

* * * * *